(12) United States Patent
Ichikawa et al.

(10) Patent No.: US 11,806,281 B2
(45) Date of Patent: Nov. 7, 2023

(54) OPHTHALMIC SURGERY INSTRUMENT

(71) Applicant: CHUKYO MEDICAL CO., INC., Nagoya (JP)

(72) Inventors: Kazuo Ichikawa, Nagoya (JP); Hiroto Toda, Nagoya (JP)

(73) Assignee: CHUKYO MEDICAL CO., INC., Nagoya (JP)

( * ) Notice: Subject to any disclaimer, the term of this patent is extended or adjusted under 35 U.S.C. 154(b) by 334 days.

(21) Appl. No.: 17/181,880

(22) Filed: Feb. 22, 2021

(65) Prior Publication Data

US 2021/0275353 A1 Sep. 9, 2021

(30) Foreign Application Priority Data

Mar. 5, 2020 (JP) .................................. 2020-037591

(51) Int. Cl.
 *A61F 9/007* (2006.01)

(52) U.S. Cl.
 CPC ...... *A61F 9/00754* (2013.01); *A61F 9/00736* (2013.01); *A61F 9/00781* (2013.01)

(58) Field of Classification Search
 CPC .............. A61F 9/00736; A61F 9/00781; A61F 9/00754; A61B 2017/32007; A61B 2217/007; A61B 2217/005; A61B 2017/32008; A61B 2017/320084; A61B 17/3203; A61M 1/77–774
 See application file for complete search history.

(56) References Cited

U.S. PATENT DOCUMENTS 3,732,858 A * 5/1973 Banko .............. A61B 17/32002
 606/107
3,776,238 A * 12/1973 Peyman .............. A61F 9/00763
 606/171
(Continued)

FOREIGN PATENT DOCUMENTS

EP 2335660 A1 * 6/2011 ......... A61F 9/00745
JP 2004520120 A 7/2004
(Continued)

OTHER PUBLICATIONS

Extended European Search Report dated Aug. 3, 2021 for corresponding EP patent application No. EP21160059.8.
(Continued)

*Primary Examiner* — Julian W Woo
*Assistant Examiner* — Osama Nemer
(74) *Attorney, Agent, or Firm* — Kenichiro Yoshida

(57) ABSTRACT

Provided is an ophthalmic surgery instrument that is capable of simplifying the structure of a rod-shaped portion, which is inserted into an eyeball during ophthalmic surgery, and that is suitable for excising a to-be-excised part of the eyeball.

The ophthalmic surgery instrument includes a rod-shaped portion that is inserted into an eyeball during ophthalmic surgery. The rod-shaped portion has a single passage formed therein so as to penetrate from one end portion thereof to another end portion thereof. A bent portion is formed at a tip end of the rod-shaped portion. A liquid is caused to flow through the passage to flow out from a tip end opening portion of the passage or a to-be-excised part is sucked through the passage while excising the to-be-excised part with the bent portion.

15 Claims, 11 Drawing Sheets

(56) References Cited

U.S. PATENT DOCUMENTS

| | | | | |
|---|---|---|---|---|
| 3,812,855 | A * | 5/1974 | Banko | A61M 1/79 137/205 |
| 3,994,297 | A * | 11/1976 | Kopf | A61F 9/00763 606/107 |
| 4,470,429 | A * | 9/1984 | Johnson | F16K 11/076 137/625.46 |
| 4,553,957 | A * | 11/1985 | Williams | A61M 1/85 604/902 |
| 4,689,040 | A * | 8/1987 | Thompson | A61B 17/22004 604/272 |
| 5,154,696 | A * | 10/1992 | Shearing | A61F 9/00745 606/171 |
| 5,364,405 | A * | 11/1994 | Zaleski | A61F 9/00745 606/107 |
| 5,569,283 | A * | 10/1996 | Green | A61B 17/320036 30/162 |
| 5,893,862 | A * | 4/1999 | Pratt | A61F 9/00763 604/22 |
| 6,135,999 | A * | 10/2000 | Fanton | A61B 17/1659 606/45 |
| 2009/0287233 | A1 * | 11/2009 | Huculak | A61F 9/00763 606/167 |
| 2019/0060119 | A1 | 2/2019 | Baerveldt et al. | |
| 2019/0209375 | A1 | 7/2019 | Mittelstein et al. | |

FOREIGN PATENT DOCUMENTS

| | | |
|---|---|---|
| JP | 2007501687 A | 2/2007 |
| JP | 5000000 B1 | 8/2012 |
| JP | 5458205 B1 | 4/2014 |
| WO | 2018151808 A1 | 8/2018 |

OTHER PUBLICATIONS

Japanese Office Action dated May 14, 2021 For the Corresponding Japanese Application JP2020-037591 With English Translation.
Japanese Office Action dated Jul. 6, 2021 For the Corresponding Japanese Application JP2020-037591 With English Translation.

* cited by examiner

FIG.12
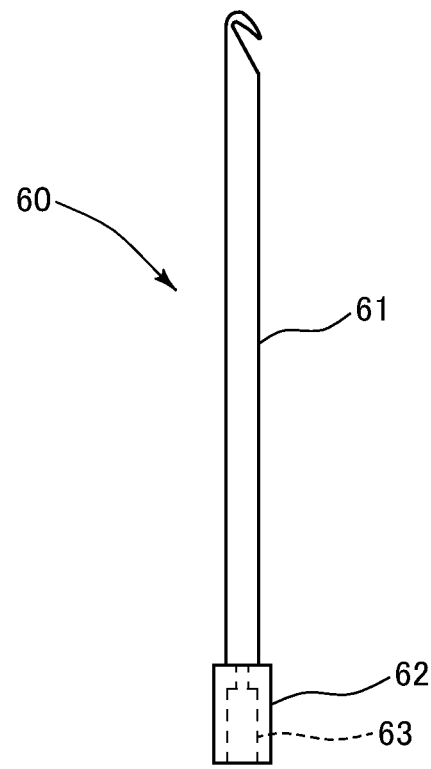
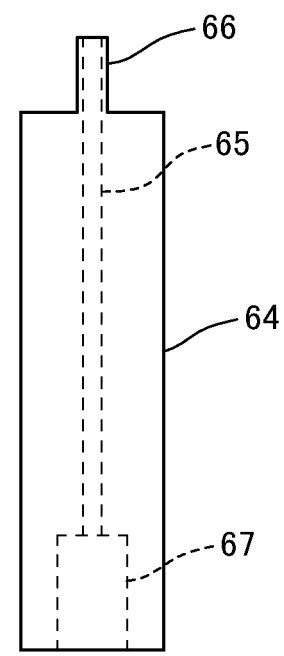

OPHTHALMIC SURGERY INSTRUMENT

RELATED APPLICATIONS

This application claims the priority of Japanese Patent Application No. 2020-037591 filed on Mar. 5, 2020, which is incorporated herein by reference.

BACKGROUND OF THE INVENTION

Field of the Invention

This disclosure relates to an ophthalmic surgery instrument.

Description of Related Art

As is well known, glaucoma is one of the major diseases of the eye and can cause blindness, so that proper treatment is essential for glaucoma. Glaucoma occurs when the intraocular pressure remains abnormally high over a long period of time, and the increase in intraocular pressure is caused by impaired outflow of aqueous humor. Therefore, for glaucoma, treatment for ensuring proper outflow of aqueous humor is given.

Treatments for glaucoma include not only prescribing medications (eye drops and oral medications), but also surgical procedures. Since abnormalities in a trabecular meshwork cause impaired outflow of aqueous humor, surgical procedures include an operation of removing the trabecular meshwork. Instruments for this operation are proposed in Japanese Patent No. 5458205 and Japanese Patent No. 5000000. Each of the instruments disclosed in Japanese Patent No. 5458205 and Japanese Patent No. 5000000 includes a rod-shaped portion (probe) that is inserted into an eyeball during ophthalmic surgery, and has an excision portion (blade portion, cutter) for excising a to-be-excised part (specifically, trabecular meshwork) of the eyeball, on the tip end side of the rod-shaped portion. Moreover, an outflow port for a cleaning liquid and a suction port for a trabecular meshwork and waste liquid are individually formed on the tip end side of the rod-shaped portion, and a passage leading to the outflow port and a passage leading to the suction port are individually formed inside the rod-shaped portion.

Each of the instruments of Japanese Patent No. 5458205 and Japanese Patent No. 5000000 has a problem that the structure of the rod-shaped portion becomes complicated in order to allow all of an excision function, a liquid outflow function, and a suction function to be activated at the same time.

Therefore, an object of this disclosure is to provide an ophthalmic surgery instrument that is capable of simplifying the structure of a rod-shaped portion, which is inserted into an eyeball during ophthalmic surgery, and that is suitable for excising a to-be-excised part of the eyeball.

SUMMARY OF THE INVENTION

In order to solve the aforementioned problem, this disclosure provides an ophthalmic surgery instrument comprising a rod-shaped portion that is inserted into an eyeball during ophthalmic surgery, has a single passage formed therein so as to penetrate from one end portion thereof to another end portion thereof, and has a bent portion formed at a tip end thereof, wherein the ophthalmic surgery instrument is used in a form in which another member is not provided in the passage, during ophthalmic surgery, and the ophthalmic surgery instrument is for causing a liquid to flow through the passage to flow out from an opening on the bent portion side, or sucking a to-be-excised part of the eyeball through the passage, while excising the to-be-excised part with the bent portion.

According to this disclosure, since the bent portion is formed at the tip end of the rod-shaped portion, by moving the rod-shaped portion in a direction that is a direction crossing the axis of the rod-shaped portion and is toward the side on which the bent portion is located, the to-be-excised part of the eyeball can be excised along this direction. In addition, during the excision, a part not to be excised that is located on the depth side in the axial direction of the rod-shaped portion can be inhibited from being damaged.

Since the single passage for liquid outflow or for suction is formed inside the rod-shaped portion, either a liquid outflow function or a suction function can be activated in addition to the excision function. For example, in the case where a liquid is caused to flow through the passage of the rod-shaped portion to flow out from the opening on the bent portion side while excising the to-be-excised part, outflow of blood can be inhibited by the pressure of the outflow liquid. In addition, for example, in the case where the to-be-excised part is sucked through the passage of the rod-shaped portion, the to-be-excised part can be inhibited from remaining within the eye. Moreover, the structure of the rod-shaped portion can be simplified as compared to the structures of the instruments of Japanese Patent No. 5458205 and Japanese Patent No. 5000000 in each of which a plurality of passages are formed in the rod-shaped portion.

A blade portion (in other words, a sharp shape) may be formed at the bent portion. According to this, the to-be-excised part can be easily excised with the bent portion.

According to one aspect of this disclosure, the passage may be used while switching between a purpose of causing the liquid to flow out and a purpose of sucking the to-be-excised part. Accordingly, all of an excision function, a liquid outflow function, and a suction function can be realized by one instrument.

According to one aspect of this disclosure, the ophthalmic surgery instrument may further include a grip portion non-detachably or detachably connected to the rod-shaped portion, on a side opposite to the side where the bent portion of the rod-shaped portion is formed. According to this, the position of the rod-shaped portion can be easily controlled by manipulating the grip portion.

According to one aspect of this disclosure, the ophthalmic surgery instrument may further include a connection portion configured to detachably connect a flow path of a liquid supply unit or a suction unit and the passage of the rod-shaped portion. According to this, the surgery instrument (the passage of the rod-shaped portion) and the liquid supply unit or the suction unit can be easily connected to each other. In addition, whether to connect the liquid supply unit or the suction unit to the surgery instrument can be selected.

According to one aspect of this disclosure, the ophthalmic surgery instrument may further include a switching portion including a first connection portion connected to the passage of the rod-shaped portion, a second connection portion connected to a flow path of a liquid supply unit, and a third connection portion connected to a flow path of a suction unit, the switching portion being configured to switch between a first state in which the first connection portion and the second connection portion communicate with each other and communication between the first connection portion and the third connection portion is blocked and a second state in which communication between the first connection portion and the second connection portion is blocked and the first connection portion and the third connection portion communicate with each other. According to this, it is possible to easily switch to the first state in which the liquid supply unit is connected to the surgery instrument or the second state in which the suction unit is connected to the surgery instrument.

According to one aspect of this disclosure, a width, in a diameter direction of the rod-shaped portion, of the bent portion may be equal to or smaller than an outer diameter of the rod-shaped portion. According to this, when inserting the rod-shaped portion into the eyeball, the tip end or the edge portion of the bent portion can be inhibited from coming into contact with the outer membrane of the eyeball. In addition, in the case where a tube member is attached to the eyeball and the rod-shaped portion is inserted into the eyeball through the tube member, a situation in which the bent portion of the rod-shaped portion cannot pass through the tube member can be inhibited, that is, the surgery instrument can be easily inserted into the eyeball through the tube member. Moreover, a small-diameter tube member can be used, and a cut formed in the eyeball when attaching the tube member to the eyeball can be small.

According to one aspect of this disclosure, the width, in the diameter direction of the rod-shaped portion, of the bent portion may be larger than the outer diameter of the rod-shaped portion. According to this, the range of the bent portion can be increased, and thus the excision function can be further improved.

According to one aspect of this disclosure, an angle between the bent portion and an extension line of a contour line extending in an axial direction of the rod-shaped portion may be larger than 90 degrees. According to this, when excising the to-be-excised part while moving the rod-shaped portion in the direction crossing the axis, the bent portion can be inhibited from coming into contact with a part not to be excised located on the depth side of the to-be-excised part. In addition, when excising the to-be-excised part while moving the rod-shaped portion, the bent portion can be inhibited from coming off the to-be-excised part.

According to one aspect of this disclosure, the angle may be equal to or smaller than 160 degrees. According to this, the bent portion can be easily brought into contact with the to-be-excised part.

According to one aspect of this disclosure, the opening on the bent portion side of the passage may be formed so as to be inclined relative to the axis of the rod-shaped portion. According to this, the opening of the passage used as a liquid outflow port or a suction port can be increased in size, so that the liquid outflow function or the suction function can be improved.

According to one aspect of this disclosure, the opening on the bent portion side of the passage may be formed so as to be perpendicular to the axis of the rod-shaped portion. According to this, in the case where a liquid is caused to flow out from the opening, the liquid is easily caused to flow out in the direction of the axis of the rod-shaped portion.

According to one aspect of this disclosure, the to-be-excised part may be a trabecular meshwork. Accordingly, while excising the trabecular meshwork with the bent portion, the liquid can be caused to flow out from the tip end of the rod-shaped portion, or the trabecular meshwork can be sucked.

BRIEF DESCRIPTION OF THE DRAWINGS

FIG. 12 is a side view of an ophthalmic surgery instrument according to a third embodiment.

DESCRIPTION OF THE PREFERRED EMBODIMENTS

First Embodiment

Figure 1:
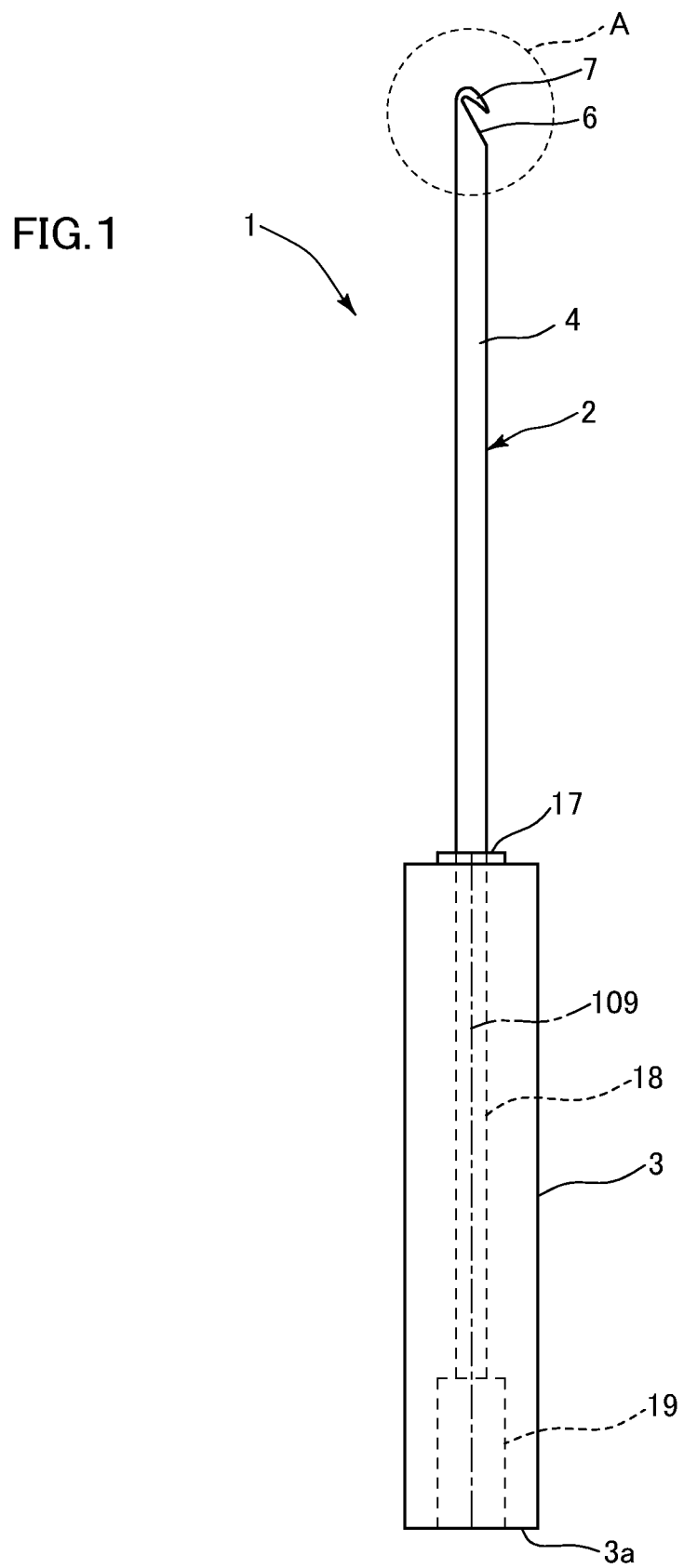
FIG. 1 is a side view of an ophthalmic surgery instrument according to a first embodiment.

Hereinafter, a first embodiment of this disclosure will be described with reference to the drawings. An ophthalmic surgery instrument 1 (hereinafter, sometimes referred to simply as instrument) shown in FIG. 1 is an instrument for excising a specific part (for example, trabecular meshwork) of an eyeball. The instrument 1 includes: a rod-shaped portion 2 that is inserted into an eyeball during ophthalmic surgery; and a grip portion 3 that is connected to a base end portion 17 of the rod-shaped portion 2 and is held by a practitioner during ophthalmic surgery.

The rod-shaped portion 2 is formed from a hard material (for example, a metal). The rod-shaped portion 2 includes: a main body portion 4 extending in a straight manner (in other words, in a rod shape); and a bent portion 7 having an angle with respect to the main body portion 4, on the tip end side of the main body portion 4. The main body portion 4 has therein a single passage 5 (see FIG. 2 and FIG. 3) that penetrates from one end portion thereof (the base end portion 17 shown in FIG. 1) to another end portion thereof (a tip end opening portion 6 shown in FIG. 1, FIG. 2, and FIG. 3) in a direction in which a central axis 100 of the main body portion 4 extends. In the rod-shaped portion 2, there is no passage other than the passage 5. The passage 5 is a passage for causing an outflow liquid to flow therethrough during ophthalmic surgery, and is a passage for sucking waste liquid or a part of an eyeball that is excised with the bent portion 7. In addition, another member (for example, a member having an excision function (a blade portion, a discharge portion, or the like), a member having a passage for liquid outflow or suction, etc.) is not provided at the passage 5. Therefore, when a liquid or a suction material flows through the passage 5, the liquid or the suction material flows through the passage 5 while being in direct contact with the inner wall of the passage 5.

A cross-section, orthogonal to the central axis 100, of a portion of the main body portion 4 other than the tip end opening portion 6 has an annular shape. That is, the cross-section is formed in a shape having: an outer peripheral line (a contour line of the main body portion 4) having a perfectly circular shape; and an inner peripheral line (a line of a wall surface of the passage 5) having a perfectly circular shape and concentric with the outer peripheral line, on the inner side of the outer peripheral line. In addition, the portion of the main body portion 4 other than the tip end opening portion 6 is formed in a shape in which the outer diameter and the inner diameter thereof do not change along the direction of the central axis 100. As described above, the main body portion 4 is formed in a cylindrical shape having a constant diameter.

The tip end opening portion 6 of the main body portion 4 is provided so as to form an opening in the direction in which the central axis 100 extends. That is, the tip end opening portion 6 is provided such that the central axis 100 crosses a region surrounded by an inner peripheral line 8 (see FIG. 3) of the tip end opening portion 6. In addition, the tip end opening portion 6 is formed so as to be inclined relative to the central axis 100. That is, in an end surface (surface surrounded by the inner peripheral line 8 and an outer peripheral line 9 of the tip end opening portion 6 in FIG. 3) forming the tip end opening portion 6, no portion orthogonal to the central axis 100 and no portion parallel to the central axis 100 are present. Here, point 6a (see FIG. 2 and FIG. 3) of the tip end opening portion 6 that is closest to the base end portion 17 side of the main body portion 4 is defined as an opening start point, and a contour line 104 (see FIG. 2 and FIG. 3) of the main body portion 4 that extends in a straight manner from the opening start point 6a so as to be parallel to the central axis 100 is defined as a first contour line. In this embodiment, as seen in the side view of FIG. 2, the inclination angle of the tip end opening portion 6 with respect to the central axis 100 is constant or substantially constant along a direction from the opening start point 6a to a boundary portion 10 (corner portion) between the tip end opening portion 6 and the bent portion 7. The inclination angle is not limited thereto and may change continuously or stepwise along the direction from the opening start point 6a to the boundary portion 10.

An angle θ1 (see FIG. 2) formed by the first contour line 104 and the surface of the tip end opening portion 6 is larger than 90 degrees and smaller than 180 degrees. The angle θ1 is an angle of the surface of the tip end opening portion 6 with respect to the first contour line 104 at the position of the opening start point 6a. Preferably, the angle θ1 is equal to or larger than 120 degrees and equal to or smaller than 160 degrees. When the angle θ1 is equal to or larger than 120 degrees, the length from the opening start point 6a of the tip end opening portion 6 through the corner portion 10 of the bent portion 7 to a tip end 13 of the bent portion 7 can be increased, so that the bent portion 7 can be easily formed in the manufacturing process for the rod-shaped portion 2. In addition, when the angle θ1 is equal to or smaller than 160 degrees, a space 150 (see FIG. 2) between the opening start point 6a and the bent portion 7 can be inhibited from becoming excessively large, so that a liquid that is caused to flow out from the tip end opening portion 6 during ophthalmic surgery is allowed to easily reach the bent portion 7, or a to-be-excised part (for example, trabecular meshwork) that is excised with the bent portion 7 is allowed to be easily sucked into the tip end opening portion 6. Even in the case where the inclination angle of the tip end opening portion 6 changes in the middle, the angle θ1 of the tip end opening portion 6 with respect to the first contour line 104 at the position of the opening start point 6a is larger than 90 degrees and smaller than 180 degrees, and preferably equal to or larger than 120 degrees and equal to or smaller than 160 degrees.

Figure 3:
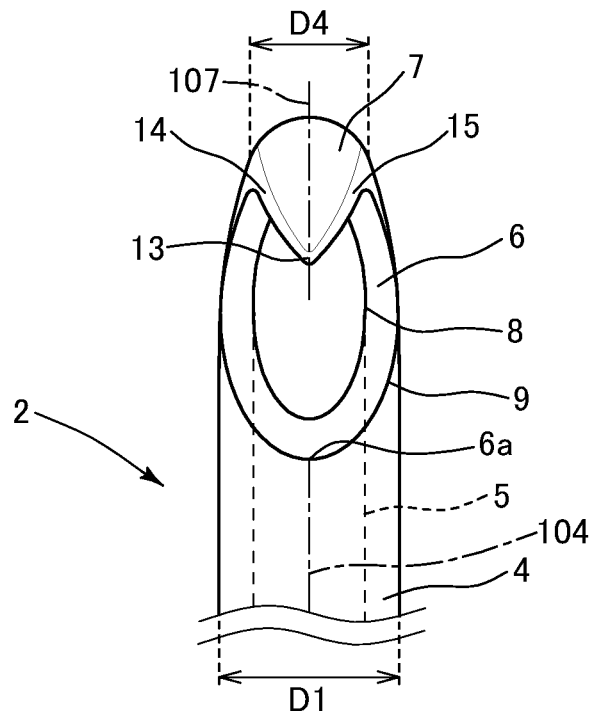
FIG. 3 is a view of the structure on the tip end side of the rod-shaped portion as seen in a direction B in FIG. 2 and is a front view of the structure on the tip end side of the rod-shaped portion.

Moreover, a blade portion (sharp shape) is formed at the entirety or a part of an edge (the inner peripheral line 8 or the outer peripheral line 9 shown in FIG. 3) of the tip end opening portion 6 (for example, a part of the tip end opening portion 6 from the boundary portion 10 between the bent portion 7 and the tip end opening portion 6). The tip end opening portion 6 is not limited thereto, and a blade portion does not have to be formed at the tip end opening portion 6. The excision function can be improved by forming a blade portion at the tip end opening portion 6 in addition to the bent portion 7. The excision function can be improved by forming a blade portion at the entirety of the tip end opening portion 6, as compared to the case where a blade portion is formed at a part of the tip end opening portion 6 or the case where a blade portion is not formed at the tip end opening portion 6. In addition, in the case where a blade portion is formed at a part of the tip end opening portion 6 or the case where a blade portion is not formed at the tip end opening portion 6, a part not to be excised (for example, Schlemm's canal, etc.) can be inhibited from being damaged.

The bent portion 7 is formed from the same material as the main body portion 4 so as to be integrated with the main body portion 4. In addition, the bent portion 7 is formed so as to be continuous with the tip end opening portion 6. That is, no portion extending so as to be parallel to the central axis 100 is present between the bent portion 7 and the tip end opening portion 6. Specifically, the bent portion 7 is provided so as to be bent in a direction approaching the first contour line 104 (in other words, the opening start point 6a or the central axis 100) such that the bending starts from an opening endpoint that is a point farthest from the opening start point 6a of the tip end opening portion 6 (in other words, the most protruding point, in the direction of the central axis 100, of the tip end opening portion 6). In other words, the bent portion 7 is provided so as to cover a part of the tip end opening portion 6 with the space 150 therebetween. In still other words, the bent portion 7 is provided so as to face the tip end opening portion 6 with the space 150 therebetween.

Figure 2:
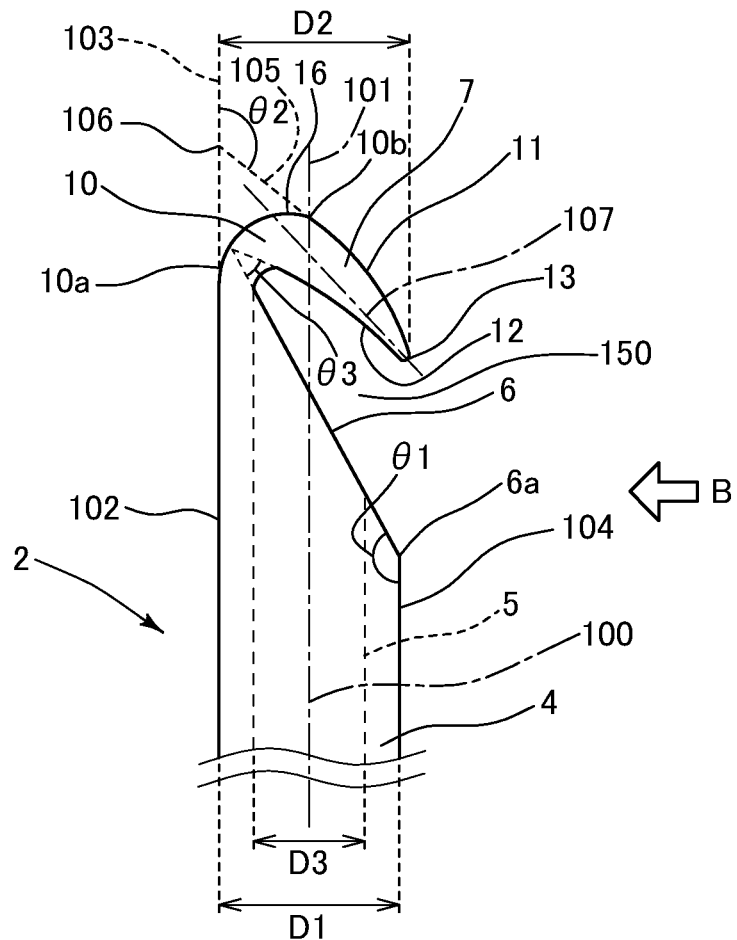
FIG. 2 is an enlarged view of part A in FIG. 1 and is a side view of a structure on the tip end side of a rod-shaped portion.

The bent portion 7 has a surface 11 (hereinafter, referred to as outer surface) continuous with the outer surface of the main body portion 4, a surface 12 (hereinafter, referred to as inner surface) continuous with the inner surface (the wall surface of the passage 5) of the main body portion 4, and edge portions 14 and 15 connecting the surfaces 11 and 12 (see FIG. 2 and FIG. 3). The outer surface 11 faces in a direction opposite to the tip end opening portion 6. The inner surface 12 faces the tip end opening portion 6. In the front view of FIG. 3, the edge portions 14 and 15 are end portions located at both ends of the bent portion 1 in a direction parallel to the diameter direction of the main body portion 4. FIG. 3 is a view as seen in a direction in which the tip end 13 of the bent portion 7 and the inclined tip end opening portion 6 face the front, among directions perpendicular to the central axis 100, and is a view as seen in a direction B in FIG. 2. FIG. 2 is a view as seen in a direction rotated by 90 degrees with respect to the direction of FIG. 3, among the directions perpendicular to the central axis 100.

The bent portion 7 is formed in a shape in which the gap between the edge portions 14 and 15 gradually decreases as approaching the tip end 13 from the corner portion 10 (boundary portion with the main body portion 4). That is, the bent portion 7 is formed in a tapered shape. In addition, the tip end 13 is formed in a shape that allows a to-be-excised part of an eyeball to be pierced, that is, in a sharp shape. In this case, the tip end 13 functions as a blade portion.

A blade portion is formed at each of the edge portions 14 and 15 of the bent portion 7. That is, each of the portions of the edge portions 14 and 15 where the blade portions are formed is formed in a sharp shape. The blade portions may be formed over the entire ranges of the edge portions 14 and 15 or may be formed over partial ranges (for example, partial ranges continuous with the tip end 13). In the case where blade portions are formed over the entire ranges of the edge portions 14 and 15 from the tip end 13 to the corner portion 10, the excision function of the instrument 1 can be improved. In the case where blade portions are formed only over parts of the ranges of the edge portions 14 and 15 from the tip end 13 to the corner portion 10, a part not to be excised (Schlemm's canal, etc.) can be inhibited from being damaged.

Here, in the side view of FIG. 2, a contour line 102 of the main body portion 4 that is located at the symmetrical position (180 degrees opposite side) of the first contour line 104 with respect to the central axis 100 and extends in a straight manner so as to be parallel to the central axis 100, is defined as a second contour line. In addition, the outer surface of the corner portion 10 (boundary portion with the main body portion 4) of the bent portion 7 is shaped so as to draw a circular arc as seen in the side view of FIG. 2, an end portion 10a, connected to the main body portion 4, of the outer surface of the corner portion 10 is defined as a corner start end portion, and an end portion 10b of the outer surface of the corner portion 10 on the side opposite to the end portion 10a is defined as a corner termination end portion.

An angle θ2 (see FIG. 2) formed by the bent portion 7 and an extension line 103 (see FIG. 2) obtained by extending the second contour line 102 from the corner start end portion 10a outwardly in the same direction as the second contour line 102 is larger than 90 degrees. The angle θ2 is an angle at the corner portion 10 of the bent portion 7 with respect to the extension line 103. Specifically, the angle θ2 is an angle formed by: a portion, on the corner termination end portion 10b side of a point of intersection 106 with the extension line 103, of a line 105 tangent to the corner termination end portion 10b in the side view of FIG. 2; and a portion, on the opposite side of the point of intersection 106 from the corner start end portion 10a, of the extension line 103. In addition, the angle θ2 is set such that portions such as the tip end 13 of the bent portion 7 do not enter the passage 5 of the main body portion 4 through the tip end opening portion 6. In other words, the angle θ2 is set such that the space 150 is formed between the bent portion 7 and the tip end opening portion 6. Specifically, the angle θ2 is set so as to be, for example, equal to or smaller than 160 degrees.

Moreover, an angle θ3 formed by the bent portion 7 and the tip end opening portion 6 as seen in the side view of FIG. 2 is larger than 0 degrees and smaller than 90 degrees. The angle θ3 is an angle formed by the outer peripheral line of the inner surface 12 (surface facing the tip end opening portion 6) of the bent portion 7 and the outer peripheral line 9 (see FIG. 3) of the tip end opening portion 6.

The bent portion 7 is provided so as to gradually approach the opening start point 6a from the corner portion 10 toward the tip end 13 as seen in the side view of FIG. 2. A most protruding portion 16 (see FIG. 2), in the direction of the axis 100 of the rod-shaped portion 2, of the bent portion 7 is located at or near the corner portion 10, and is located at a position different from that of the tip end 13. In addition, a portion, closest to the opening start point 6a, of the bent portion 7 is the tip end 13. Moreover, the bent portion 7 extends in a straight manner or in a substantially straight manner from the corner portion 10 to the tip end 13. That is, when a line 107 that passes through the middle between the outer surface 11 and the inner surface 12 of the bent portion 7 and extends from the corner portion 10 toward the tip end 13 in the side view of FIG. 2 is defined as a bent portion center line, the bent portion center line 107 extends in a straight manner or in a substantially straight manner. The bent portion center line 107 is a line that passes through the middle between the edge portions 14 and 15, which are located at both ends of the bent portion 7 in the direction parallel to the diameter direction of the main body portion 4, as seen in the front view of FIG. 3. The bent portion center line 107 is not limited to a line extending in a straight manner or in a substantially straight manner, and may extend in a curved manner.

Figure 4:
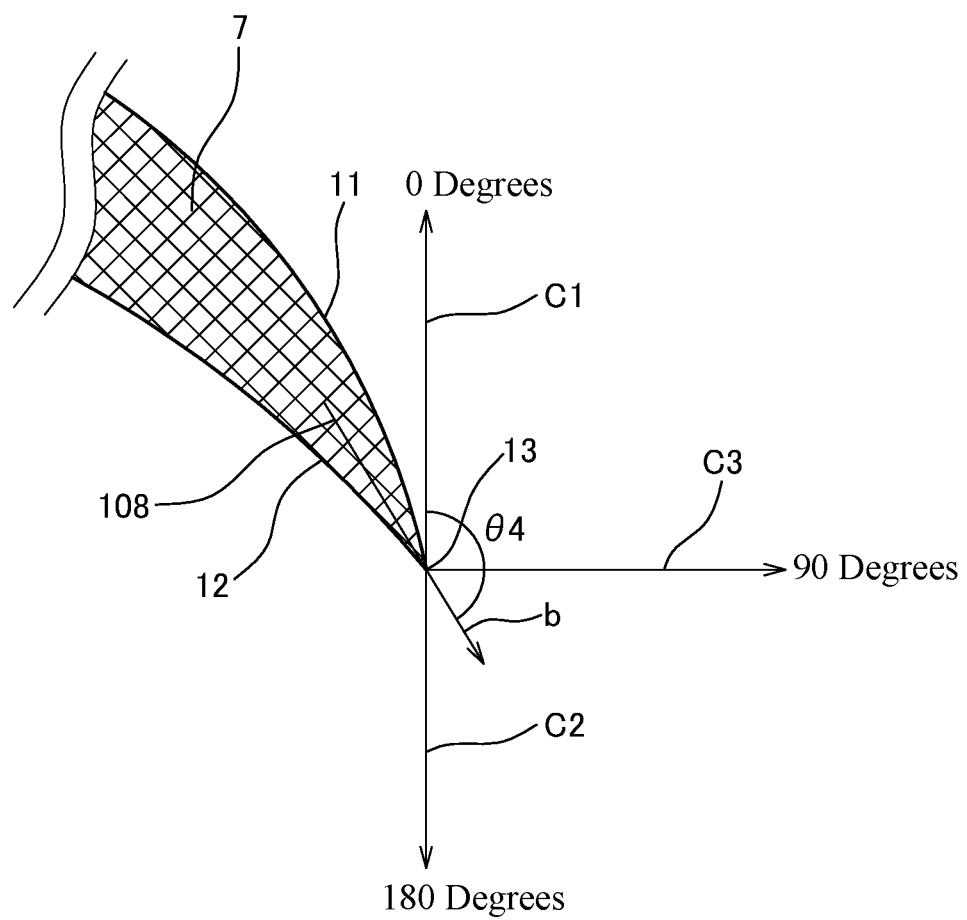
FIG. 4 is a cross-sectional view of a part on the tip end side of a bent portion.

In the cross-sectional view of FIG. 4, when the tip end 13 of the bent portion 7 is defined as an origin, a direction C1 that is the same as a direction from the base end portion 17 to the tip end opening portion 6, of directions in which the central axis 100 of the main body portion 4 extends, is defined as 0 degrees, a direction C2 opposite to the direction C1 is defined as 180 degrees, and a direction C3 away from the corner portion 10 among directions perpendicular to the direction C1 is defined as 90 degrees, an angle θ4 of a direction b in which the tip end 13 is directed, with respect to the direction C1, is larger than 90 degrees. That is, the tip end 13 is directed in a direction approaching the tip end opening portion 6. In addition, the angle θ4 is set to a value smaller than 180 degrees, and is preferably equal to or smaller than 160 degrees. When the angle θ4 is equal to or smaller than 160 degrees, the tip end 13 can be easily brought into contact with a to-be-excised part. The direction b of the tip end 13 is the direction of a straight line 108 that passes through the middle between the outer surface 11 and the inner surface 12, which form the sharp shape of the tip end 13 of the bent portion 7, in the cross-sectional view of FIG. 4. The cross-section of FIG. 4 is a cross-section obtained by cutting the bent portion 7 along a plane that is parallel to the central axis 100 of the main body portion 4 and includes the bent portion center line 107.

In the side view of FIG. 2, the tip end 13 of the bent portion 7 may be located at the same position as an outer diameter D1 (see FIG. 2) of the main body portion 4 or inward of the outer diameter D1 in the diameter direction of the main body portion 4 (direction perpendicular to the central axis 100), or may be located outward of the outer diameter D1. That is, a width D2 (see FIG. 2) from the corner portion 10 to the tip end 13 of the bent portion 7 in the direction parallel to the diameter direction of the main body portion 4 may be equal to or smaller than the outer diameter D1 of the main body portion 4, or may be larger than the outer diameter D1. In the case where the width D2 is equal to or smaller than the outer diameter D1 (in other words, the case where the tip end 13 is located at a position of the outer diameter D1 or inward thereof), a small-diameter tube member 300 can be used when inserting the rod-shaped portion 2 into an eyeball through the tube member 300 in FIG. 7 described later, and a cut formed in the eyeball when attaching the tube member 300 to the eyeball can be small. On the other hand, in the case where the width D2 is larger than the outer diameter D1 (in other words, the case where the tip end 13 is located outward of the outer diameter D1), the range of the bent portion 7 can be increased, and thus the excision function can be further improved. In the case where the width D2 is larger than the outer diameter D1, when a tube member having an inner diameter larger than the width D2 of the bent portion 7 is used as the tube member 300 in FIG. 7 described later, the rod-shaped portion 2 can be inserted into an eyeball through the tube member 300.

As seen in the side view of FIG. 2, the tip end 13 may be located on the side farther from the corner portion 10 than an extension line 101 obtained by extending the central axis 100 from the tip end opening portion 6 outwardly, or may be located on the side closer to the corner portion 10 than the extension line 101. In the case where the tip end 13 is located on the side farther from the corner portion 10 than the extension line 101, the bent portion 7 serving as a blade portion can be increased in size, and thus it becomes easier to excise a to-be-excised part of an eyeball. On the other hand, in the case where the tip end 13 is located on the side closer to the corner portion 10 than the extension line 101, the range where the tip end opening portion 6 is covered by the bent portion 7 can be reduced, and thus it becomes easier to perform liquid outflow from the tip end opening portion 6 or suction into the tip end opening portion 6.

The tip end 13 may be located inward or outward of an inner diameter D3 (see FIG. 2) of the main body portion 4 (which is also the diameter of the passage 5) in the diameter direction of the main body portion 4.

In the front view of FIG. 3, a width D4 of the bent portion 7 in the direction parallel to the diameter direction of the main body portion 4 is equal to or smaller than the outer diameter D1 of the main body portion 4. Accordingly, a small-diameter tube member 300 can be used when inserting the rod-shaped portion 2 into an eyeball through the tube member 300 in FIG. 7 described later, and a cut formed in the eyeball when attaching the tube member 300 to the eyeball can be small. The width D4 refers to the maximum width from one edge portion 14 to the other edge portion 15 of the bent portion 7.

In instrument 1, another tubular member that covers the outside of the rod-shaped portion 2 is not provided. That is, the rod-shaped portion 2 is not a member disposed within another tubular member, but is a member provided so as to be exposed to the outside.

Referring back to FIG. 1, the grip portion 3 is non-detachably connected to the rod-shaped portion 2 by integral molding, press fitting, an adhesive, or the like. The grip portion 3 is formed from, for example, a resin. The grip portion 3 is formed in a rod shape having an outer diameter larger than the outer diameter D1 (see FIG. 2 and FIG. 3) of the main body portion 4. A central axis 109 of the grip portion 3 is located on the same straight line as the central axis 100 of the rod-shaped portion 2. The grip portion 3 has therein a passage 18 that penetrates from one end portion thereof to another end portion thereof in the direction of the axis 109 of the grip portion 3. The passage 18 is provided so as to communicate with the passage 5 of the rod-shaped portion 2.

The grip portion 3 has a connection portion 19 that is detachably connected to another flow path, on the side opposite to the side connected to the rod-shaped portion 2. The connection portion 19 is formed as a recess that is recessed from an end surface 3a of the grip portion 3 on the side opposite to the side connected to the rod-shaped portion 2. The connection portion 19 communicates with the passage 18. Instead of the connection portion 19 which is a recess, the grip portion 3 may include a connection portion that is a projection projecting from the end surface 3a of the grip portion 3.

Figure 5:
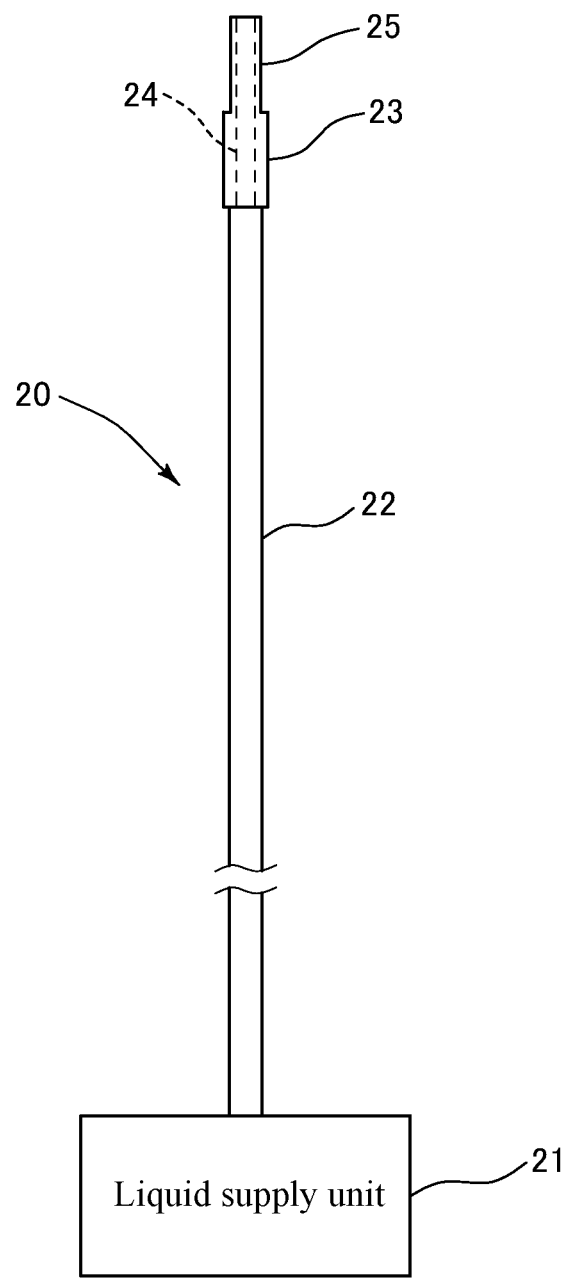
FIG. 5 is a schematic configuration diagram of a liquid supply device.
Figure 6:
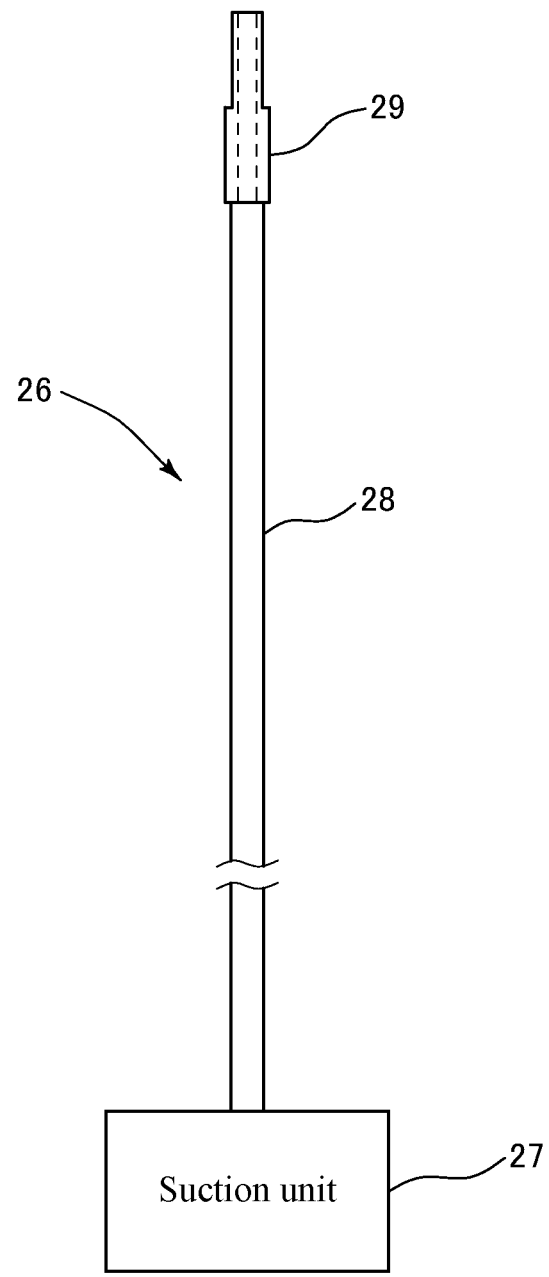
FIG. 6 is a schematic configuration diagram of a suction device.

The instrument 1 in FIG. 1 is used in a form in which the instrument 1 is connected to a liquid supply device 20 shown in FIG. 5 or a suction device 26 shown in FIG. 6, during ophthalmic surgery. The liquid supply device 20 in FIG. 5 includes: a liquid supply unit 21 that controls supply of a liquid (cleaning liquid, water, or the like) to be supplied into an eyeball during ophthalmic surgery; a tube 22 that is connected at one end thereof to the liquid supply unit 21 and forms a flow path for guiding an outflow liquid from the liquid supply unit 21; and a connection portion 23 that is connected to an end portion of the tube 22 on the side opposite to the side connected to the liquid supply unit 21 and detachably connects to another flow path. The liquid supply unit 21 is composed of a pump or the like that sucks in and discharges a liquid contained in a liquid-containing unit (not shown). The liquid supply unit 21 has, for example, a function of monitoring the pressure in an eyeball (the pressure at which a liquid is supplied into the eyeball), and supplies the liquid into the eyeball through the tube 22 and the instrument 1 connected to the tube 22, such that this pressure is maintained constant. The tube 22 is formed from, for example, a flexible material. The connection portion 23 is formed in a tubular shape. That is, the connection portion 23 has therein a passage 24 that penetrates from one end portion thereof to another end portion thereof. The passage 24 is provided so as to communicate with the flow path of the tube 22. The connection portion 23 has a projection 25 that projects in the axial direction thereof. The instrument 1 and the liquid supply device 20 are connected to each other by fitting the projection 25 into the recess 19 (connection portion) of the grip portion 3. In the case where the connection portion of the grip portion 3 is formed as a projection, the connection portion of the liquid supply device 20 is formed as a recess.

The suction device 26 in FIG. 6 includes: a suction unit 27 that controls suction (in other words, generates a suction force); a tube 28 that is connected at one end thereof to the suction unit 27 and forms a flow path for guiding a suction material entering the tube 28 through another end thereof, toward the suction unit 27; and a connection portion 29 that is connected to an end portion of the tube 28 on the side opposite to the side connected to the suction unit 27 and detachably connects to another flow path. The suction unit 27 is composed of a pump or the like that generates suction air. The tube 28 is formed from, for example, a flexible material. The connection portion 29 is formed in the same shape as the connection portion 23 in FIG. 5. The instrument 1 and the suction device 26 are connected to each other by fitting the connection portion 29 into the recess 19 of the grip portion 3.

The liquid supply device 20 and the suction device 26 may be provided as an integrated device or as separate devices. In addition, the liquid supply device 20 and the suction device 26 may be devices used for surgery other than glaucoma surgery (for example, vitreous surgery). The instrument 1 and the liquid supply device 20 or the suction device 26 connected thereto form an ophthalmic surgery apparatus.

The instrument 1 is used, for example, in an operation of excising a trabecular meshwork in a surgical procedure of glaucoma. Giving a description with reference to a schematic diagram of the structure of an eye shown in FIG. 7, aqueous humor is generated in the ciliary body located at a lower part of the illustration of an iris 204 of the eye. Normally, this aqueous humor flows into an anterior chamber 201 of the eye through a pupil and then flows out from a corner located in the circumferential direction of the anterior chamber 201. There area trabecular meshwork 202 and a Schlemm's canal 203 at the corner. The trabecular meshwork 202 acts as a filter that restricts outflow of the aqueous humor. The Schlemm's canal 203 has a structure for the aqueous humor to flow out. A portion indicated by the reference numeral "205" in FIG. 7 indicates a crystalline lens.

When the trabecular meshwork 202 becomes abnormally deformed or malfunctions, the flow of the aqueous humor flowing out from the anterior chamber 201 is restricted. Accordingly, the intraocular pressure increases abnormally, resulting in glaucoma. The instrument 1 is an effective instrument in a surgical procedure for this glaucoma. An example of a surgical method using the instrument 1 is as follows.

Figure 7:
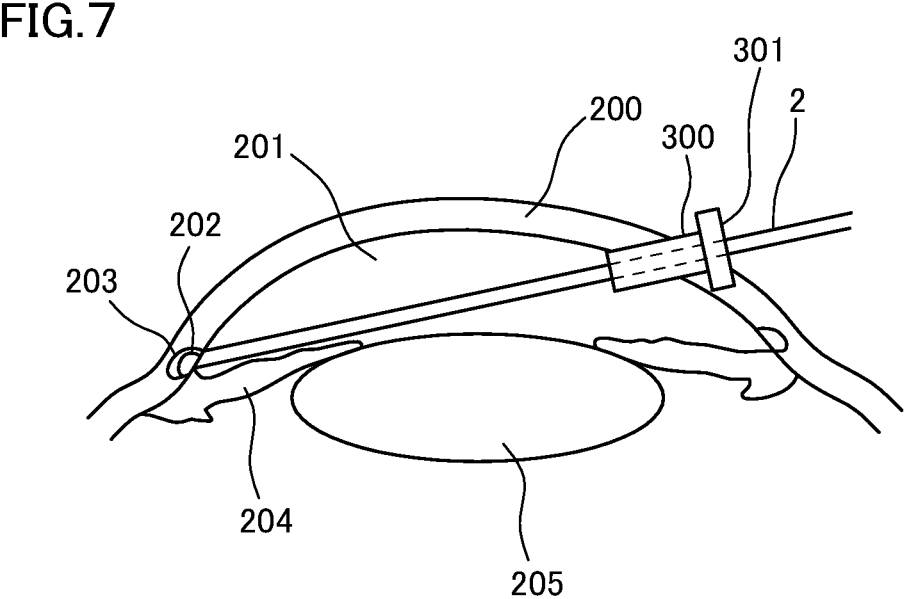
FIG. 7 is a diagram showing the overview of the structure of the anterior segment of an eye and also showing a state of an operation of excising a trabecular meshwork using the ophthalmic surgery instrument.

In preparation for surgery, a microscope is tilted by 30 to 45 degrees toward the practitioner side and the patient's head is also positioned such that the trabecular meshwork 202 can be seen from the front through a gonioscope. Thereafter, the tube member 300 (also called trocar or cannula) for providing communication between the inside and the outside of the eyeball is attached to a cornea 200 as shown in FIG. 7. The tube member 300 has, for example, a check valve 301 that prevents backflow of the aqueous humor from the inside of the eyeball to the outside.

Thereafter, the practitioner holds the grip portion 3 of the instrument 1 and inserts the rod-shaped portion 2 into the anterior chamber 201 through the tube member 300. The tube member 300 does not have to be attached to the cornea 200. In this case, the cornea 200 may be incised with a knife, and the rod-shaped portion 2 may be inserted into the anterior chamber 201 through the incised portion.

It is noted that a connection between the instrument 1 and the liquid supply device 20 in FIG. 5 or the suction device 26 in FIG. 6 may be made in advance before inserting the rod-shaped portion 2 into the anterior chamber 201, or may be made after inserting the rod-shaped portion 2 into the anterior chamber 201.

Figure 8:
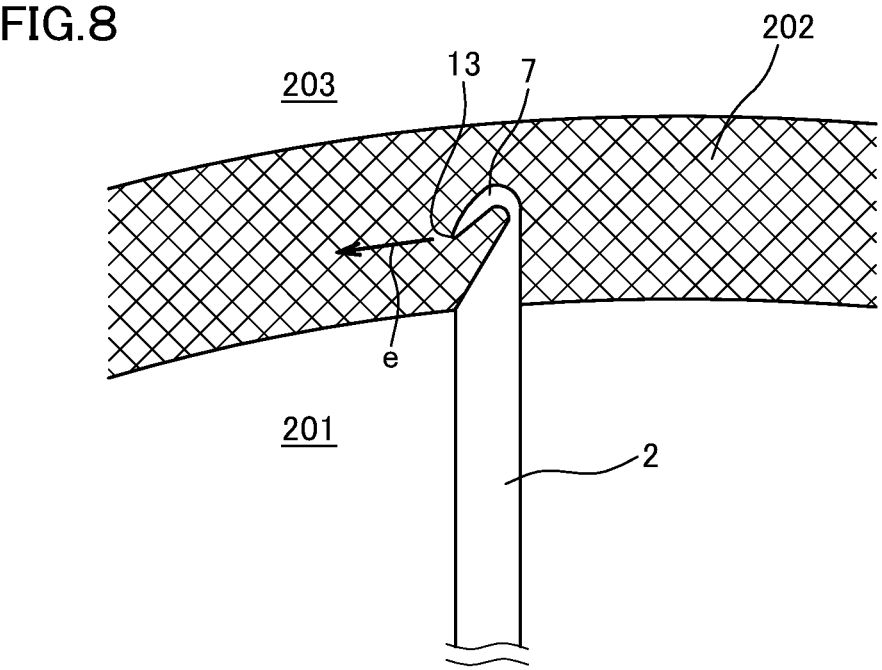
FIG. 8 is a diagram showing a state of excising the trabecular meshwork with the bent portion while moving the rod-shaped portion in a direction crossing the axis of the rod-shaped portion.
Figure 9:
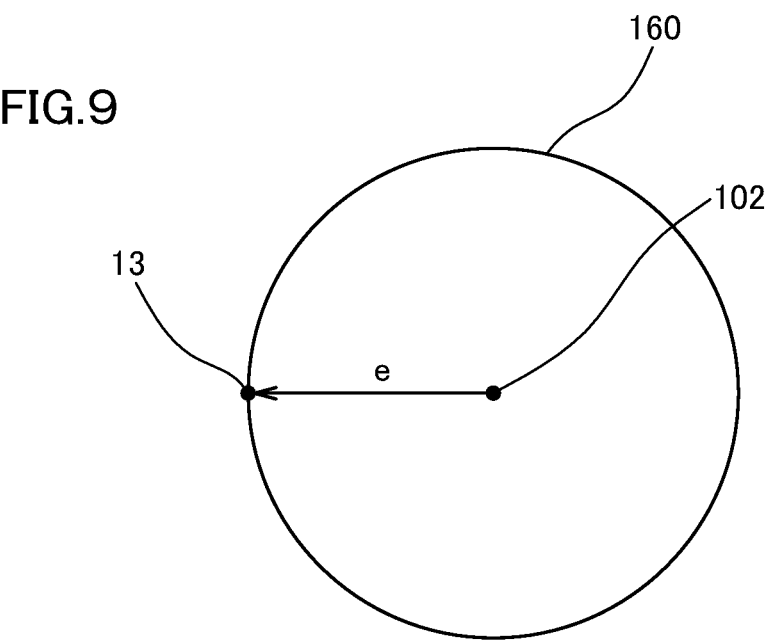
FIG. 9 is a diagram illustrating the movement direction of the rod-shaped portion when excising a to-be-excised part and is a diagram showing the direction in which the tip end of the bent portion is located in a circle centered on a contour line parallel to the central axis of the rod-shaped portion.

After the rod-shaped portion 2 is inserted into the anterior chamber 201, the bent portion 7 at the tip end of the rod-shaped portion 2 is placed at the trabecular meshwork 202. Thereafter, the trabecular meshwork 202 is excised with the blade portions formed at the bent portion 7 and the tip end opening portion 6. Specifically, the bent portion 7 is inserted into the trabecular meshwork 202 while piercing the trabecular meshwork 202 with the tip end 13 of the bent portion 7 to form a cut that serves as a trigger for excision. Thereafter, as shown in FIG. 8, the rod-shaped portion 2 is moved in a direction e that is a direction crossing the central axis 100 and is toward the tip end 13 side as seen from the corner portion 10 of the bent portion 7, thereby excising the trabecular meshwork 202 along the direction e. At this time, by moving the rod-shaped portion 2 in the direction e, the trabecular meshwork 202 is cut with the bent portion 7, and the cut trabecular meshwork 202 is also pulled out to the near side (the anterior chamber 201 side in FIG. 8) while being guided by the inner surface of the bent portion 7 and the inclined tip end opening portion 6 continuous with the inner surface of the bent portion 7. In other words, the direction e is the direction in which the tip end 13 of the bent portion 7 is located in a circle 160 centered on the above second contour line 102 (see FIG. 2) of the rod-shaped portion 2 as shown in FIG. 9. FIG. 9 is a plan view perpendicular to the second contour line 102.

Also, along with the excision of the trabecular meshwork 202, a liquid is caused to flow out from the rod-shaped portion 2, or the trabecular meshwork 202 is sucked into the rod-shaped portion 2. Specifically, for example, a connection between the instrument 1 and the liquid supply device 20 in FIG. 5 is made, and the liquid supply unit 21 is actuated while excising the trabecular meshwork 202 with the instrument 1, thereby causing a liquid (cleaning liquid, water, or the like) to flow out from the tip end opening portion 6. By the outflow of this liquid, the pressure of the anterior chamber 201 can be maintained, and outflow of blood to the anterior chamber 201 can be inhibited. Accordingly, the practitioner can be allowed to easily grasp where the trabecular meshwork 202 is located in the anterior chamber 201, and thus can be allowed to easily excise the trabecular meshwork 202, thereby inhibiting apart other than the trabecular meshwork 202 from being excised.

After the trabecular meshwork 202 is excised, for example, a connection between the instrument 1 and the suction device 26 in FIG. 6 is made in place of the connection between the instrument 1 and the liquid supply device 20. At this time, in a state where the rod-shaped portion 2 is still inserted in the anterior chamber 201, the connection between the instrument 1 and the liquid supply device 20 may be replaced with a connection between the instrument 1 and the suction device 26, or, in a state where the rod-shaped portion 2 is pulled out from the anterior chamber 201, the connection between the instrument 1 and the liquid supply device 20 may be replaced with a connection between the instrument 1 and the suction device 26. Then, the suction unit 27 is actuated while placing the bent portion 7 within the range where the trabecular meshwork 202 has been excised, thereby sucking (collecting) the remaining trabecular meshwork 202 and waste liquid after the excision through the passage 5 in the instrument 1 into the suction device 26. At the time of this suction, a liquid for maintaining the intraocular pressure may be supplied to the anterior chamber 201 by using an instrument (instrument having the same shape as that of the instrument 1 or having a shape different from that of the instrument 1) different from the instrument 1 used for the suction. Accordingly, during suction, blood can be inhibited from flowing out to the anterior chamber 201, so that it becomes easier to suck the trabecular meshwork 202.

The above-described method is an example in which after a connection between the instrument 1 and the liquid supply device 20 is made and the trabecular meshwork 202 is excised, the connection between the instrument 1 and the liquid supply device 20 is replaced with a connection between the instrument 1 and the suction device 26 and suction is performed. Instead of this, a connection between the instrument 1 and the suction device 26 is made from the beginning, and the trabecular meshwork 202 may be sucked into the instrument 1 at the same time as the trabecular meshwork 202 is excised with the instrument 1. In this case, during excision and suction of the trabecular meshwork 202 by the instrument 1, a liquid for maintaining the intraocular pressure may be supplied to the anterior chamber 201 by using an instrument (instrument having the same shape as that of the instrument 1 or having a shape different from that of the instrument 1) different from the instrument 1 used for the excision and the suction.

Since, as described above, the instrument 1 according to this embodiment has the bent portion 7 at the tip end thereof, and a blade portion is formed at the bent portion 7, the trabecular meshwork 202 formed along the circumferential direction of the anterior chamber 201 can be easily excised along the circumferential direction. In addition, since the bending angle θ2 (see FIG. 2) of the bent portion 7 is larger than 90 degrees, and the angle θ4 (see FIG. 4) of the direction of the tip end 13 of the bent portion 7 is also larger than 90 degrees, damage to the Schlemm's canal 203 (see FIG. 8), which is located on the depth side of the trabecular meshwork 202, due to the blade portion (including the tip end 13) of the bent portion 7 coming into contact with the Schlemm's canal 203 can be inhibited. Moreover, the bent portion 7 can be inhibited from coming off the trabecular meshwork 202 when excising the trabecular meshwork 202 while moving the rod-shaped portion 2.

Since the angle θ2 of the bent portion 7 is, for example, equal to or smaller than 160 degrees, it is easier to bring the blade portion (including the tip end 13) of the bent portion 7 into contact with the to-be-excised part (trabecular meshwork 202) as compared to the case where the angle θ2 of the bent portion 7 is larger than 160 degrees. In addition, the space 150 between the bent portion 7 and the tip end opening portion 6 can be ensured, or, in other words, the space 150 in which the to-be-excised part is hooked by the bent portion 7 can be easily ensured.

Since the tip end opening portion 6 is formed so as to be inclined relative to the central axis 100, the tip end opening portion 6 can be made larger as compared to the case where the tip end opening portion 6 is formed so as to be perpendicular to the central axis 100. Accordingly, the liquid outflow function from the tip end opening portion 6 or the suction function into the tip end opening portion 6 can be improved. In addition, since the tip end opening portion 6 is formed so as to be inclined, the bent portion 7 can be easily formed.

By providing the tip end opening portion 6 so as to form an opening in the direction in which the central axis 100 extends, the tip end opening portion 6 is provided at a position facing the bent portion 7. Accordingly, in the case where the tip end opening portion 6 is used as a liquid outflow port, a liquid can be easily supplied from the tip end opening portion 6 toward the bent portion 7, and the pressure around the bent portion 7 can be maintained, so that outflow of blood around the bent portion 7 can be inhibited. In addition, in the case where the tip end opening portion 6 is used as a suction port, a to-be-excised part excised with the bent portion 7 can be easily sucked into the tip end opening portion 6.

Since the single passage 5 is formed in the rod-shaped portion 2 and used as a passage for causing a liquid to flow out or a passage for suction, it is possible to provide the excision instrument 1 having a liquid outflow function or a suction function with a simple structure.

Since the instrument 1 includes the connection portion 19 which detachably connects the passage 5 and another flow path, a connection between the instrument 1 and the liquid supply device 20 or the suction device 26 can be easily made. In addition, during surgery, the device connected to the instrument 1 can be switched from the liquid supply device 20 to the suction device 26 or from the suction device 26 to the liquid supply device 20. That is, the passage 5 can be used as both a passage for causing a liquid to flow out and a passage for suction.

Second Embodiment

Figure 10:
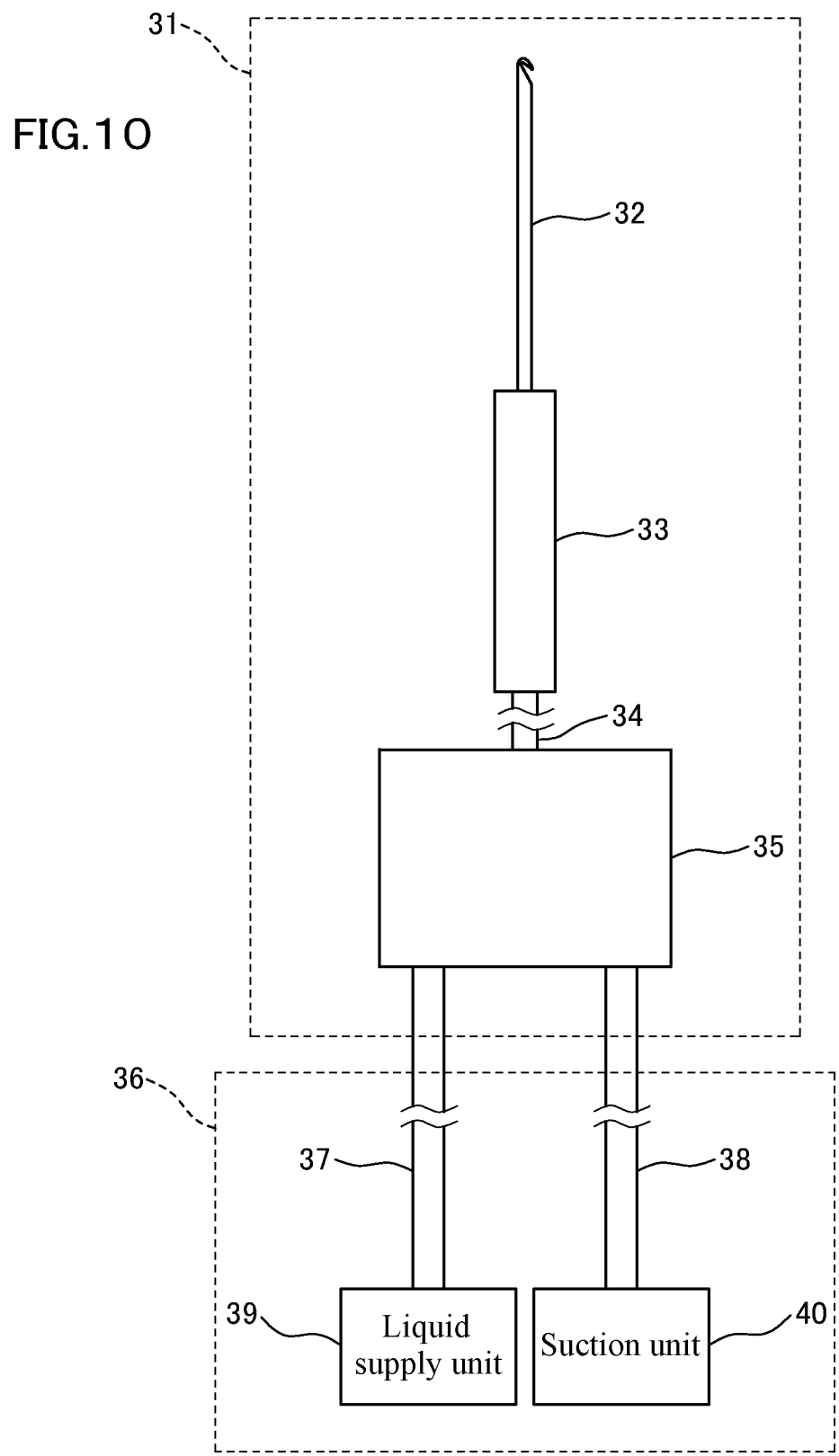
FIG. 10 is a schematic configuration diagram of an ophthalmic surgery instrument according to a second embodiment and an external device connected thereto.

Next, a second embodiment of this disclosure will be described focusing on the differences from the above embodiment. FIG. 10 shows a schematic configuration diagram of an ophthalmic surgery instrument 31 (hereinafter, sometimes referred to simply as instrument) according to the second embodiment and an external device 36 connected thereto.

The instrument 31 includes a rod-shaped portion 32, a grip portion 33, a tube 34, and a switching portion 35. The rod-shaped portion 32 is a portion that is inserted into an eyeball during ophthalmic surgery, and has the same shape as that of the rod-shaped portion 2 (see FIG. 2 and FIG. 3) of the first embodiment. The grip portion 33 is a portion that is connected to a base end portion of the rod-shaped portion 32 and is held by a practitioner during ophthalmic surgery. The grip portion 33 is formed in a tubular shape having a larger diameter than the rod-shaped portion 32 and having therein a passage that communicates with a passage of the rod-shaped portion 32. The grip portion 33 may be non-detachably connected to the rod-shaped portion 32 similar to the first embodiment, or may be detachably connected to the rod-shaped portion 32 similar to a third embodiment described later.

The tube 34 is a portion that is connected at one end thereof to the grip portion 33 and connected at another end thereof to the switching portion 35 to form a flow path between the switching portion 35 and the grip portion 33. The tube 34 is formed from, for example, a flexible material. The tube 34 may be omitted, and the grip portion 33 and the switching portion 35 may be directly connected to each other.

Figure 11:
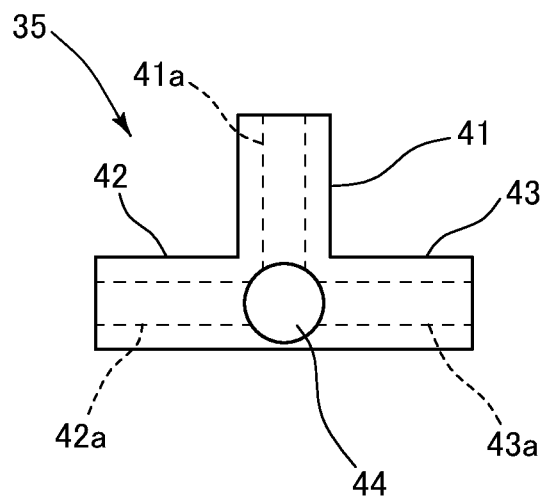
FIG. 11 is a schematic diagram of a switching portion.

The switching portion 35 is a portion that switches a flow path caused to communicate with the passage of the rod-shaped portion 32 among a plurality of external flow paths. The switching portion 35 is configured, for example, as a manual or electric three-way valve. FIG. 11 illustrates a manual switching portion 35. The switching portion 35 in FIG. 11 has a first connection portion 41, a second connection portion 42, and a third connection portion 43. The connection portions 41 to 43 have therein flow paths 41a to 43a, respectively. The switching portion 35 has a manipulation portion 44 for switching flow paths to be caused to communicate with each other and a flow path to be blocked among the three flow paths 41a to 43a. The manipulation portion 44 is configured to be switchable to any of a plurality of manipulation positions including: a first manipulation position (first state) at which the flow path 41a of the first connection portion 41 and the flow path 42a of the second connection portion 42 communicate with each other and the flow path 43a of the third connection portion 43 is blocked; and a second manipulation position (second state) at which the flow path 41a of the first connection portion 41 and the flow path 43a of the third connection portion 43 communicate with each other and the flow path 42a of the second connection portion 42 is blocked. The manipulation positions of the manipulation portion 44 may include a third manipulation position at which all the three flow paths 41a to 43a are blocked. The manipulation portion 44 is configured such that, for example, a rotation manipulation is performed thereon by a user.

The first connection portion 41 is detachably connected to the tube 34 in FIG. 10. That is, the flow path 41a of the first connection portion 41 is detachably connected to the passage of the rod-shaped portion 32 via the passages of the tube 34 and the grip portion 33. The flow path 42a of the second connection portion 42 is detachably connected to a flow path 37 of a liquid supply unit 39 of the external device 36 in FIG. 10. The flow path 43a of the third connection portion 43 is detachably connected to a flow path 38 of a suction unit 40 of the external device 36. The switching portion 35 (the second connection portion 42 and the third connection portion 43) corresponds to a connection portion that detachably connects the flow path 37 or 38 of the liquid supply unit 39 or the suction unit 40 and the passage of the rod-shaped portion 32.

When the manipulation portion 44 is at the first manipulation position, the instrument 31 and the liquid supply unit 39 communicate with each other, and communication between the instrument 31 and the suction unit 40 is blocked. When the manipulation portion 44 is at the second manipulation position, the instrument 31 and the suction unit 40 communicate with each other, and communication between the instrument 31 and the liquid supply unit 39 is blocked.

The switching portion 35 may be configured such that the state of the switching portion 35 is electrically switched. In this case, the switching portion 35 can be configured, for example, as a solenoid valve.

The external device 36 in FIG. 10 includes: the liquid supply unit 39 that is the same as the liquid supply unit 21 in FIG. 5; the suction unit 40 that is the same as the suction unit 27 in FIG. 6; a tube 37 (flow path) that is connected at one end thereof to the liquid supply unit 39 and connected at another end thereof to the second connection portion 42; and a tube (flow path) that is connected at one end thereof to the suction unit 40 and connected at another end thereof to the third connection portion 43.

Similar to the first embodiment, the instrument 31 is used, for example, in an operation of excising a trabecular meshwork. In addition, the instrument 31 is used in a form in which the instrument 31 is connected to the external device 36 as shown in FIG. 10. At this time, for example, first, the switching portion 35 is brought into the first state, and a trabecular meshwork is excised with the bent portion (blade portion) at the tip end of the rod-shaped portion 32 while causing a liquid to flow out from the tip end of the rod-shaped portion 32. Accordingly, the trabecular meshwork can be excised while inhibiting outflow of blood. Thereafter, the switching portion 35 is brought into the second state with the rod-shaped portion 32 still inserted in the anterior chamber, and the excised trabecular meshwork is sucked into the rod-shaped portion 32 to be collected. For example, by repeating switching between the first state and the second state, liquid outflow and suction may be repeated while excising the trabecular meshwork.

As described above, in this embodiment, the same effects as those of the first embodiment are achieved, and the flow path caused to communicate with the passage of the rod-shaped portion 32 can also be easily switched between the liquid supply unit 39 and the suction unit 40 by the switching portion 35. Accordingly, for example, it is possible to frequently switch between liquid outflow and suction while excising the trabecular meshwork.

Third Embodiment

Next, a third embodiment of this disclosure will be described focusing on the differences from the above embodiments. In the first embodiment, the example in which the rod-shaped portion and the grip portion are non-detachably connected to each other has been described. However, in the third embodiment, an example in which the rod-shaped portion and the grip portion are configured to be attachable to and detachable from each other will be described.

FIG. 12 shows an ophthalmic surgery instrument 60 (hereinafter, sometimes referred to simply as instrument) according to the third embodiment. The instrument 60 includes a rod-shaped portion 61, a connection portion 62 that is connected to a base end portion of the rod-shaped portion 61, and a grip portion 64 that is attachable to and detachable from the connection portion 62. The rod-shaped portion 61 is a portion that is inserted into an eyeball during ophthalmic surgery, and has the same shape as that of the rod-shaped portion 2 (see FIG. 2 and FIG. 3) of the first embodiment.

The connection portion 62 has a recess 63 that communicates with a passage of the rod-shaped portion 61. The grip portion 64 is formed in a rod shape having a larger diameter than the rod-shaped portion 61. The grip portion 64 has therein a passage 65 that penetrates from one end portion thereof to another end portion thereof in the axial direction of the grip portion 64. The grip portion 64 has, at one end portion thereof, a projection 66 that projects in the axial direction. The projection 66 is a connection portion that detachably connects to the connection portion 62. By fitting the projection 66 into the recess 63 of the connection portion 62, the rod-shaped portion 61 and the grip portion 64 are connected to each other such that the passage of the rod-shaped portion 61 and the passage 65 of the grip portion 64 communicate with each other.

The grip portion 64 has, at an end portion on the side opposite to the projection 66, a connection portion 67 that detachably connects the passage 65 of the grip portion 64 to an external flow path. The connection portion 67 is formed as a recess that is recessed from the end portion of the grip portion 64, but may be formed as a projection. The connection portion 67 is detachably connected to the liquid supply device 20 in FIG. 5 or the suction device 26 in FIG. 6.

Similar to the first and second embodiments, the instrument 60 is used, for example, in an operation of excising a trabecular meshwork. In this case, surgery is performed in the same procedure as in the first embodiment or the second embodiment in a state where the rod-shaped portion 61 and the grip portion 64 are connected to each other.

In this embodiment, the same effects as those of the above first and second embodiments are achieved. In addition, since the rod-shaped portion 61 and the grip portion 64 are attachable to and detachable from each other, the rod-shaped portion 61 can be replaced with another rod-shaped portion 61 while sharing the grip portion 64.

Fourth Embodiment

Next, a fourth embodiment of this disclosure will be described focusing on the differences from the above embodiments. In the first embodiment, the example in which the tip end opening portion of the rod-shaped portion is formed so as to be inclined relative to the axis of the rod-shaped portion has been described. However, in the fourth embodiment, an example in which the tip end opening portion is formed so as to be perpendicular to the axis of the rod-shaped portion will be described.

Figure 13:
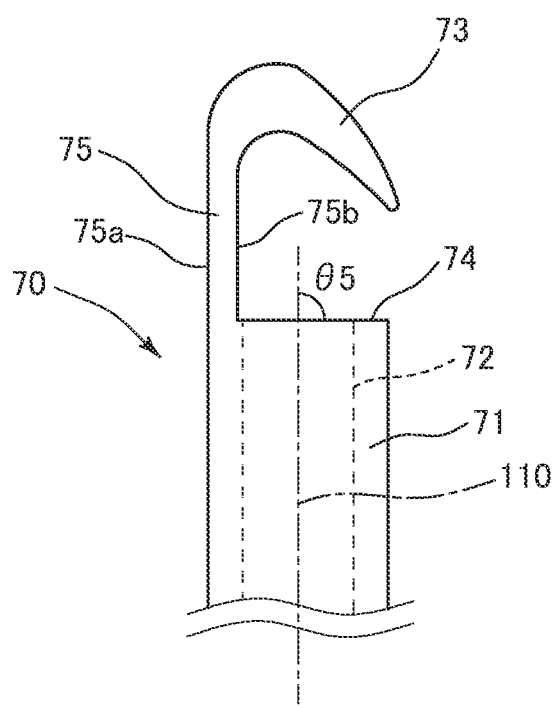
FIG. 13 is a view of a part on the tip end side of a rod-shaped portion according to a fourth embodiment as seen from the lateral side.

FIG. 13 shows a view of a part on the tip end side of the rod-shaped portion according to the fourth embodiment as seen from the lateral side (the same direction as in FIG. 2). A rod-shaped portion 70 in FIG. 13 includes: a main body portion 71 extending in a straight manner; a bent portion 73 having an angle with respect to the main body portion 71, on the tip end side of the main body portion 71; and an intermediate portion 75 located between the main body portion 71 and the bent portion 73. Similar to each of the above embodiments, the main body portion 71 has therein a single passage 72 for liquid outflow or for suction. A tip end opening portion 74 of the main body portion 71 is formed so as to be perpendicular to a central axis 110 of the main body portion 71. That is, an angle θ5 formed by the central axis 110 and the tip end opening portion 74 is 90 degrees.

The bent portion 73 is formed in the same shape as that of the bent portion 7 (see FIG. 1 to FIG. 4) of the first embodiment. The intermediate portion 75 is formed in a shape in which the intermediate portion 75 extends so as to be parallel to the central axis 110. An outer surface 75a of the intermediate portion 75 is continuous with the outer surface of the main body portion 71 and the outer surface of the bent portion 73. An inner surface 75b of the intermediate portion 75 is continuous with the inner surface (wall surface of the passage 72) of the main body portion 71 and the inner surface of the bent portion 73. The length, in a direction parallel to the central axis 110, of the intermediate portion 75 is shorter than the length, in the direction parallel to the central axis 110, of the main body portion 71.

An ophthalmic surgery instrument including the rod-shaped portion 70 according to this embodiment is used in the same manner as in the first embodiment.

As described above, in this embodiment, since the tip end opening portion 74 is formed so as to be perpendicular to the central axis 110, in the case where a liquid is caused to flow out from the tip end opening portion 74, the outflow direction of the liquid can be a direction in which the central axis 110 extends, and the outflow liquid can be efficiently supplied to the bent portion 73 side. The fourth embodiment is an embodiment in which the angle θ1 in FIG. 2 is not limited to an angle larger than 90 degrees and may be 90 degrees.

(Modifications)

This disclosure is not limited to the above embodiments, and various modifications may be made. In the above embodiments, the example in which the ophthalmic surgery instrument is used in an operation of excising a trabecular meshwork has been described, but the ophthalmic surgery instrument may be used for other ophthalmic surgery.

In the above embodiments, the example in which the angle (angle θ2 in FIG. 2) of the bent portion at the tip end of the rod-shaped portion is larger than 90 degrees has been described, but this angle may be larger than 0 degrees and equal to or smaller than 90 degrees. Even in this case, a to-be-excised part can be easily excised along a direction crossing the axis of the rod-shaped portion (in other words, the circumferential direction) as compared to the case where the tip end of the rod-shaped portion has a straight shape (that is, no bent portion is formed).

In the above first embodiment, the example in which the tip end opening portion of the rod-shaped portion is formed so as to be inclined relative to the axis has been described, but the surface of the tip end opening portion may include a portion perpendicular or parallel to the axis. Even in this case, it is possible to provide an excision instrument having a liquid outflow function or a suction function with a simple structure.

In the above embodiments, the example in which the main body portion of the rod-shaped portion has a cylindrical shape has been described, but the main body portion may have a tubular shape (for example, a square pipe shape having a quadrangular cross section cut by a plane perpendicular to the central axis) other than a cylindrical shape.

In the above embodiments, the example in which a blade portion (sharp shape) is formed at the bent portion at the tip end of the rod-shaped portion has been described, but a blade portion does not have to be formed at the bent portion. A trabecular meshwork can be peeled off (excised) even with the bent portion having no blade portion. That is, depending on the to-be-excised part, even the bent portion having no blade portion can be caused to serve as a portion (excision portion) for excising the to-be-excised part.

In FIG. 3, the example in which the gap between the edge portions 14 and 15 of the bent portion 7 gradually decreases as approaching the tip end 13 is shown, but the edge portions 14 and 15 are not limited thereto. For example, the edge portions 14 and 15 may be parallel to each other. In addition, in FIG. 3, the example in which the tip end 13 of the bent portion 7 is formed in a sharp shape is shown, but the tip end 13 does not have to be sharp, that is, may be formed so as to draw a curve.

In the above embodiments, the example in which the passage of the grip portion extends in a straight manner on the same straight line as the passage of the rod-shaped portion has been described. However, the passage of the grip portion may be provided at any position or in any shape as long as the passage of the grip portion communicates with the passage of the rod-shaped portion.

DESCRIPTION OF THE REFERENCE CHARACTERS 1, 31, 60 ophthalmic surgery instrument
2, 32, 61, 70 rod-shaped portion
3, 33, 64 grip portion
5, 72 passage of rod-shaped portion
6, 74 tip end opening portion
7, 73 bent portion
14, 15 edge portion (blade portion) of bent portion
13 tip end (blade portion) of bent portion

What is claimed is:

1. An ophthalmic surgery instrument comprising:
a rod shaped portion for inserting into an eyeball during ophthalmic surgery having a single tubular structure having a central axis and extending from a proximal end portion to a distal end portion along the central axis to provide a passage;
an opening located at the distal end portion of the rod shaped portion for discharging a liquid and for aspirating a to-be-excised part of the eyeball through the passage, the opening having an area at a predetermined first slant angle with respect to the central axis of the rod-shaped portion; and
a tapered bent portion located distal of the opening at the distal end portion and extending back towards the proximal end portion of the rod-shaped portion beyond the distal end portion at a predetermined second slant angle with respect to the opening.

2. The ophthalmic surgery instrument according to claim 1, wherein a blade portion is formed at the bent portion.

3. The ophthalmic surgery instrument according to claim 1, wherein the passage is used for switching between discharging the liquid and aspirating the to-be-excised part.

4. The ophthalmic surgery instrument according to claim 1, further comprising a grip portion non-detachably or detachably connected to a proximal side of the rod-shaped portion, opposite to a side where the bent portion of the rod-shaped portion is formed.

5. The ophthalmic surgery instrument according to claim 1, further comprising a switch including a first flow path connected to the passage of the rod-shaped portion, a second flow path connected to a flow path of a liquid supply tank, and a third flow path connected to a flow path of a suction device, the switch being configured to switch between a first state in which the first flow path and the second flow path communicate with each other and communication between the first flow path and the third flow path is blocked and a second state in which communication between the first flow path and the second flow path is blocked and the first flow path and the third flow path communicate with each other.

6. The ophthalmic surgery instrument according to claim 1, wherein a width of the bent portion, in a diameter direction of the rod shaped portion, is equal to or smaller than an outer diameter of the rod-shaped portion.

7. The ophthalmic surgery instrument according to claim 1,
wherein a point of the opening that is closest to a base end portion side of the rod-shaped portion is defined as an opening start point,
the bent portion is provided so as to gradually approach the opening start point toward a tip end of the bent portion,
a portion, closest to the opening start point, of the bent portion is the tip end of the bent portion.

8. The ophthalmic surgery instrument according to claim 1, wherein a point of the opening that is closest to a base end portion side of the rod-shaped portion is defined as an opening start point,
a contour line of the rod-shaped portion that extends in a straight manner from the opening start point so as to be parallel to the central axis is defined as a first contour line,
a contour line of the rod-shaped portion that is located at the symmetrical position of the first contour line with respect to the central axis and extends in a straight manner so as to be parallel to the central axis, is defined as a second contour line,
an angle between the bent portion and an extension line of the second contour line is larger than 90 degrees.

9. The ophthalmic surgery instrument according to claim 8, wherein the angle is equal to or smaller than 160 degrees.

10. The ophthalmic surgery instrument according to claim 1, wherein the opening on a distal end of the passage is formed so as to be inclined relative to the central axis of the rod-shaped portion,
a point of the opening that is closest to a base end portion side of the rod-shaped portion is defined as an opening starting point,
an inclination angle of the opening with respect to the central axis is constant along a direction from the opening start point to a boundary portion between the opening and the bent portion.

11. The ophthalmic surgery instrument according to claim 1, wherein the opening on a distal end of the passage is formed so as to be perpendicular to the central axis of the rod-shaped portion.

12. The ophthalmic surgery instrument according to claim 1, wherein the to-be-excised part is a trabecular meshwork.

13. The ophthalmic surgery instrument according to claim 10, wherein an angle formed by the bent portion and the opening is larger than 0 degrees and smaller than 90 degrees.

14. The ophthalmic surgery instrument according to claim 1, wherein the bent portion has an outer surface continuous with an outer surface of the rod-shaped portion, an inner surface continuous with an inner surface of the rod-shaped portion, and edge portions connecting the outer surface and the inner surface of the bent potion,
the bent portion is formed in a shape in which a gap between the edge portions gradually decreases as approaching a tip end of the bent portion.

15. An ophthalmic surgery instrument comprising:
a rod shaped portion for inserting into an eyeball during ophthalmic surgery having a single tubular structure having a central axis and extending from a proximal end portion to a distal end portion along the central axis to provide a passage;
an opening having an outer peripheral line and located at the distal end portion of the rod-shaped portion for discharging a liquid and for aspirating a to-be-excised part of the eyeball through the passage, the opening having an area at a predetermined first slant angle with respect to the central axis of the rod-shaped portion; and
a bent portion having an inner surface and located distal of the opening at the distal end portion and extending back towards the proximal end portion of the rod-shaped portion over the opening, wherein a predetermined less-than-90-degree angle is formed between the inner surface and the central axis of the rod-shaped portion.

\* \* \* \* \*